United States Patent
Schoendorf et al.

(10) Patent No.: US 8,862,247 B2
(45) Date of Patent: Oct. 14, 2014

(54) DEVICE FOR ELECTROSTIMULATION THERAPY OF THE HUMAN BODY

(75) Inventors: Erhard Schoendorf, Wadgassen (DE); Michael Schoendorf, Wadgassen (DE); Thomas Schoendorf, Losheim am See (DE)

(73) Assignees: Robert Ley, Clemency (LU); Ralf Scherer, Heusweiler (DE)

( * ) Notice: Subject to any disclaimer, the term of this patent is extended or adjusted under 35 U.S.C. 154(b) by 0 days.

(21) Appl. No.: 13/500,973

(22) PCT Filed: Oct. 8, 2010

(86) PCT No.: PCT/DE2010/001201
§ 371 (c)(1),
(2), (4) Date: Jun. 19, 2012

(87) PCT Pub. No.: WO2011/042014
PCT Pub. Date: Apr. 14, 2011

(65) Prior Publication Data
US 2012/0271395 A1 Oct. 25, 2012

(30) Foreign Application Priority Data
Oct. 10, 2009 (DE) .......................... 10 2009 048 950

(51) Int. Cl.
*A61N 1/00* (2006.01)
*A61B 5/04* (2006.01)
*A61N 1/32* (2006.01)

(52) U.S. Cl.
CPC ....................................... *A61N 1/323* (2013.01)
USPC ............ 607/148; 600/372; 600/393; 607/115

(58) Field of Classification Search
CPC .. A61N 1/0476; A61N 1/048; A61N 1/36185
USPC ........................... 600/372, 393; 607/115, 148
See application file for complete search history.

(56) References Cited

U.S. PATENT DOCUMENTS

| | | | |
|---|---|---|---|
| 5,272,624 A * | 12/1993 | Gisser et al. | 600/547 |
| 2005/0267546 A1 | 12/2005 | Parramon et al. | |
| 2007/0142878 A1 * | 6/2007 | Krulevitch et al. | 607/54 |
| 2008/0147146 A1 | 6/2008 | Wahlgren et al. | |

FOREIGN PATENT DOCUMENTS

| | | |
|---|---|---|
| DE | 2 136 297 | 1/1973 |
| DE | 36 07 077 | 9/1987 |
| DE | 38 13 838 | 5/1989 |
| WO | WO 2007/138595 | 12/2007 |

OTHER PUBLICATIONS

International Search Report of PCT/DE2010/001201, Feb. 9, 2011.

* cited by examiner

*Primary Examiner* — Nicole F Lavert
(74) *Attorney, Agent, or Firm* — Collard & Roe, P.C.

(57) ABSTRACT

The invention relates to a device for the electrostimulation therapy of the human body, comprising several electrodes (1) that contact the body surface and apparatuses (3-5) for applying voltage to the electrodes (1). According to the invention, the electrodes are arranged in a line and the apparatuses are provided to apply voltage to the electrodes (1) consecutively along the line.

14 Claims, 3 Drawing Sheets

DEVICE FOR ELECTROSTIMULATION THERAPY OF THE HUMAN BODY

CROSS REFERENCE TO RELATED APPLICATIONS

Figure 1:
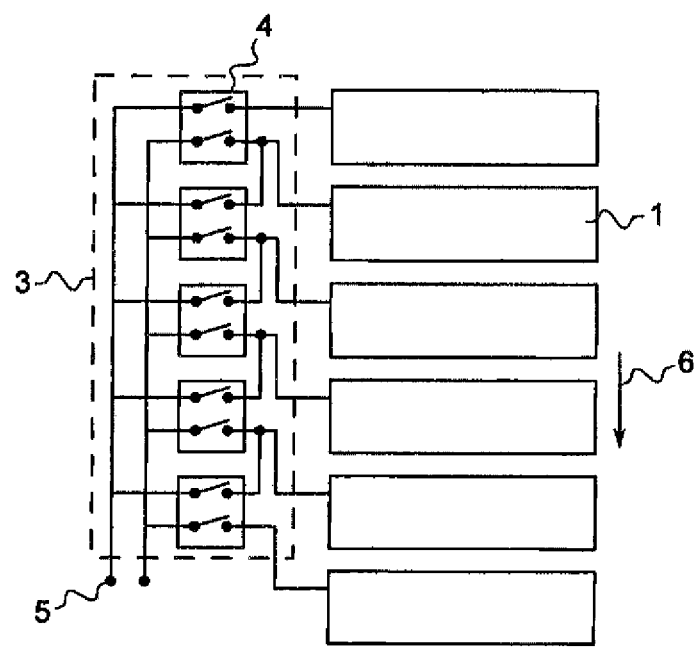

This application is the National Stage of PCT/DE2010/001201 filed on Oct. 8, 2010, which claims priority under 35 U.S.C. §119 of German Application No. 10 2009 048 950.9 filed on Oct. 10, 2009, the disclosure of which is incorporated by reference. The international application under PCT article 21(2) was not published in English.

The invention relates to a device for electrostimulation therapy of the human body, having multiple electrodes that contact the body surface, and apparatuses for applying voltage to the electrodes.

Devices of this type, using sponge electrodes, adhesive electrodes, or suction electrodes, for example, have become known by their use. The regions of the body that can be treated at the same time by means of these known devices are relatively limited. For simultaneous treatment of larger regions, multiple individual circuits that are separately adjustable are required. The use of movable electrodes that are guided over a larger region of the body surface is time-consuming and cost-intensive. In particular, it requires auxiliary personnel. Self-treatment of the spinal column, above all, cannot be performed using conventional devices.

The invention is based on the task of creating a new device of the type mentioned initially, which allows electrostimulation therapy of larger body regions with reduced effort.

The device according to the invention that accomplishes this task is characterized in that the electrodes are arranged in a row and that the stated apparatuses are provided for applying voltage to the electrodes that run consecutively in the row.

It is advantageous that it is possible to treat a larger body region at the same time by means of the device according to the invention, in that individual sections of this region have stimulation current flowing through them, in a revulsive direction, whereby the stimulation current periodically recurs in the individual sections.

While a stimulation current can flow in the horizontal direction, the electrodes are arranged at a vertical distance from one another in a preferred embodiment of the invention, so that stimulation current flows through consecutive body sections that lie one above the other.

In a preferred embodiment of the invention, the stated apparatus is provided for consecutively applying voltage to electrodes that follow one another directly in the row, whereby in particular, voltage is consecutively applied, by the stated apparatus, to pairs of electrodes that follow one another directly in the row. In other words, the voltage is applied between electrodes of the row, in each instance.

Alternatively, a common counter-electrode is assigned to the electrodes arranged in the row, which counter-electrode is provided, in particular, for placement on a body part surface that lies opposite the row arrangement.

Preferably, the advancing frequency of the voltage application is adjustable. If necessary, the voltage level can also be adjustable.

It is practical if the electrodes are disposed on a common carrier film, whereby in particular, strip electrodes are provided, which run parallel to one another with the longitudinal edges. Aside from metallic conductors, the electrodes can have sponge material that can be saturated with conductive liquid, for example water, by way of which material they lie against the body surface.

Figure 2:
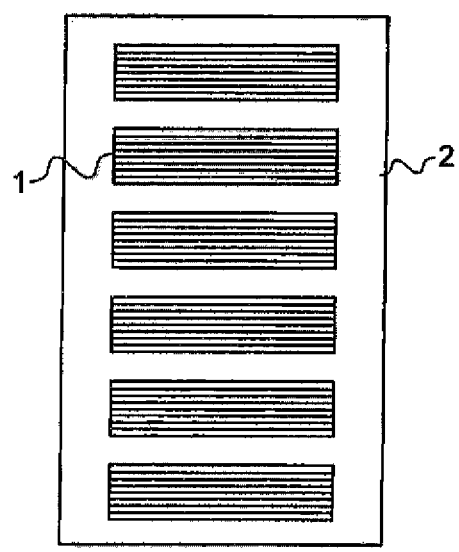
Figure 3:
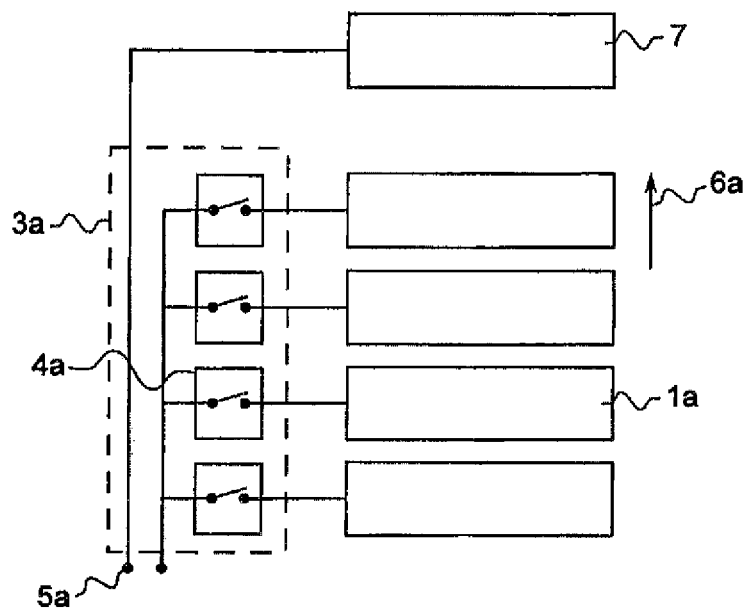
Figure 4:
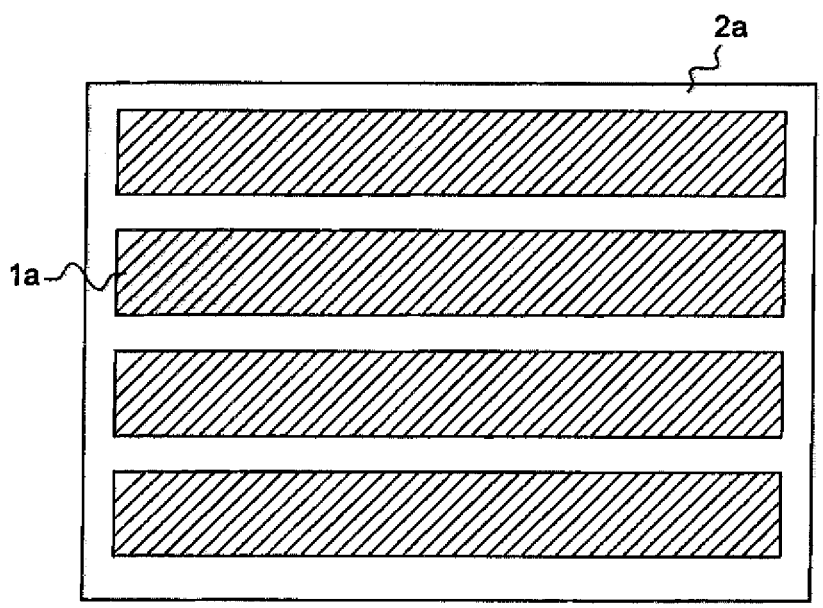
Figure 5:
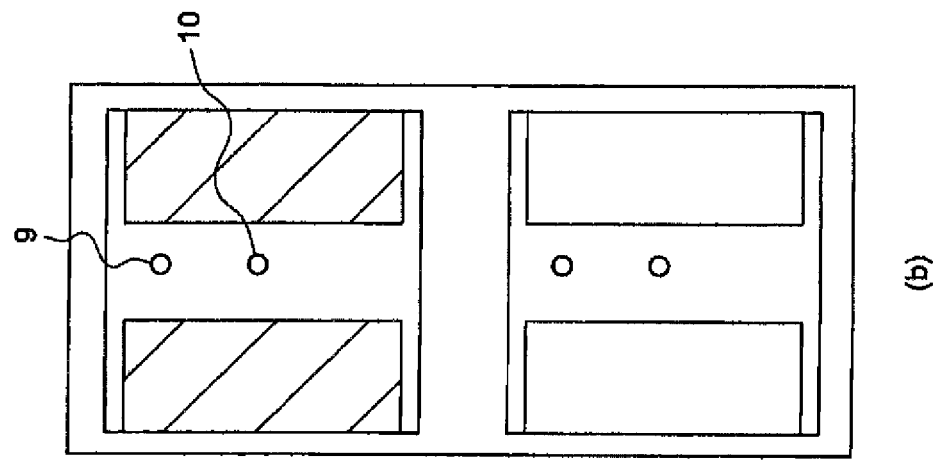
Figure 5:
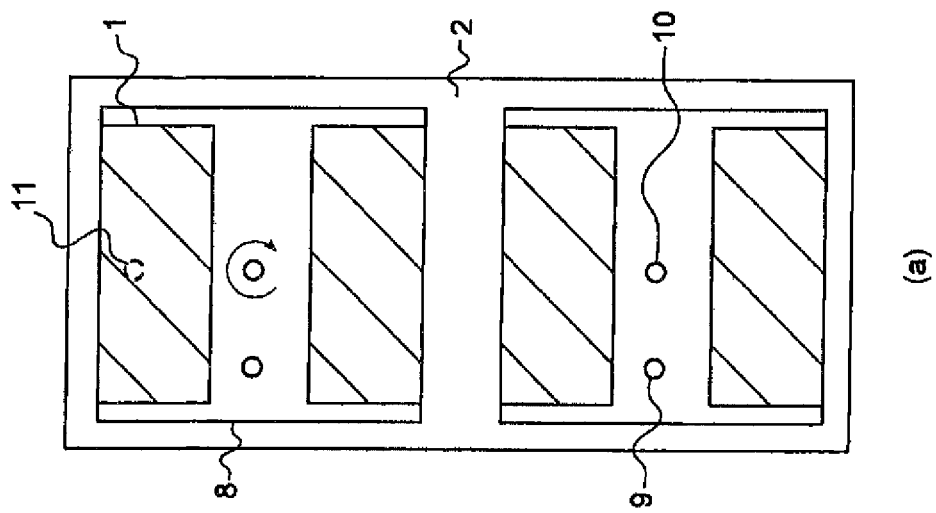

The invention will be explained in greater detail below, using exemplary embodiments and the attached drawings that relate to these exemplary embodiments. These show:

FIG. 1 a circuit schematic according to a first exemplary embodiment, for a device according to the invention for electrostimulation therapy, FIG. 2 an electrode arrangement used in the device of FIG. 1, FIG. 3 a circuit schematic according to a second exemplary embodiment, for a device according to the invention for electrostimulation therapy, FIG. 4 an electrode arrangement used in the device of FIG. 3, and FIG. 5 another electrode arrangement that can be used in a device according to the invention.

An exemplary embodiment of a device for electrotherapy of the human body shown in FIGS. 1 and 2 comprises six electrodes 1 arranged in a row, which are attached to a carrier film 2 that is common to them, for example using snaps. The strip-shaped electrodes have a length of 14 cm and a width of 5 cm in the exemplary embodiment shown. The distance between the electrodes amounts to 2 cm. Corresponding to the dimensions of the electrode arrangement, the carrier film has dimensions of 40 cm ×18 cm.

The electrodes 1 comprise not only metallic conductors but also an absorbent sponge material that can be saturated with a conductive liquid, for example water.

Each of the electrodes 1 stands in connection with a switching apparatus 3 that comprises switching elements 4, by way of which apparatus a voltage U applied to contacts 5 can be consecutively applied to the electrodes 1.

In the case being considered, the voltage U is an alternating voltage with a base frequency of 0.1 Hz, whereby the voltage component that has this base frequency has a further voltage component with a frequency of 30 Hz superimposed on it.

For treatment of the spinal column, the electrode arrangement shown in FIG. 2 is placed vertically on the back, with its longitudinal sides, and held in a desired position between the back and the back of a chair or armchair, for example, by pressing against it. No help from other persons is required for this.

The switching apparatus 3, after it is put into operation, applies the voltage U first to the uppermost of the electrodes 1 and then to the electrode that follows it. The voltage U is then advanced to the following pairs of adjacent electrodes 1, so that different height regions of the spinal column are consecutively exposed to a stimulation current, from top to bottom, in accordance with arrow 6. After voltage is applied to the two bottommost electrodes, advancing starts from the top again.

The advancing frequency is adjustable. The time of switching through from top to bottom, in each instance, can be selected to be between 1 second and 20 seconds, In the following figures, parts that are the same or have the same effect are indicated with the same reference number as in the preceding figures, whereby the letter a or b is added to the reference number in question.

A device for electrostimulation therapy of the human body shown in FIGS. 3 and 4 differs from the previous device in that, among other things, not six but only four electrodes 1a are affixed to a common carrier film 2a. The length of the electrodes 1a amounts to 28 cm, at a width of 5 cm. Corresponding to the dimensions of the electrode arrangement, the carrier film has dimensions of 31.5 cm×24 cm in this exemplary embodiment.

The device of FIGS. 3 and 4 furthermore comprises, in contrast to the preceding device, a counter-electrode 7 that is common to the electrodes 1*a*. A voltage U that is applied to contacts 5*a* can be transmitted to the counter-electrode 7 and one of the electrodes 1*a*, in each instance, by way of a switching apparatus 3*a*. The voltage U can be advanced from electrode to electrode, according to arrow 6*a*, by way of the switching apparatus 3.

For electrostimulation therapy, the electrode arrangement shown in FIG. 4 can be placed against the abdomen with the four electrodes 1*a*, and the counter electrode 7 can be placed against the back, opposite the electrodes 1*a*. When the voltage that is applied between the counter-electrode and the electrode 1*a*, in each instance, from bottom to top, is advanced, a stimulation current flows through the body in correspondingly changing height regions. Thus, the entire lower abdomen region can be treated using this device, in a rising direction.

FIG. 5 shows an electrode arrangement with a carrier film 2*b* and four electrodes 1*b*, two of which are affixed to an intermediate film 8, in each instance. The intermediate film 8 is attached to the carrier film 2 by way of snaps 9 and 10. After the snap 9 is released, the intermediate film 8 can be rotated around the snap 10, so that the electrodes 1*b* assume the position shown in FIG. 5*b*, in which they are oriented vertically. The intermediate film 8 can be fixed in place on the carrier film 2*b* again, at 11 in the rotational position shown in FIG. 5*b*, by way of the snap 9.

The invention claimed is:

1. Device for electrostimulation therapy of the human body, having multiple electrodes (1) configured to contact the body surface, and apparatuses (3-5) for applying voltage to the electrodes (1), wherein the electrodes (1) are arranged in a row and the apparatuses (3-5) comprise a switching apparatus configured for applying a voltage to the electrodes (1) consecutively in the row.

2. Device according to claim 1, wherein the electrodes (1) are arranged at a vertical distance from one another.

3. Device according to claim 2, wherein the voltage is applied from top to bottom (6) or from bottom to top (6*a*).

4. Device according to claim 1, wherein the stated apparatuses (3-5) are configured for consecutive application of voltage to the electrodes (1) that follow one another directly in the row.

5. Device according to claim 1, wherein pairs of the electrodes (1) that follow one another directly in the row can have the voltage consecutively applied to them by means of the stated apparatuses (3-5).

6. Device according to claim 1, wherein the electrodes (1*a*) that are arranged in the row have a common counter-electrode (7) assigned to them.

7. Device according to claim 6, wherein the counter-electrode (7) is provided for placement on a body part surface that lies opposite the row arrangement.

8. Device according to claim 1, wherein advancing of the voltage application and, if applicable, the voltage level are adjustable.

9. Device according to claim 1, wherein the electrodes (1) are arranged on a common carrier film (2).

10. Device according to claim 1, wherein the electrodes (1) are strip electrodes having longitudinal sides arranged parallel to one another.

11. Device according to claim 1, wherein the electrodes (1) comprise a sponge material that can be saturated with a conductive liquid.

12. Device according to claim 9, wherein a position and location on the carrier film of each of the electrodes (1*b*) is adjustable.

13. Device according to claim 12, wherein the electrodes (1*b*) can be rotated on the carrier film (2*b*), particularly by 90°.

14. Device according to claim 12, wherein multiple electrodes (1*b*) are arranged on an intermediate film (8) and the intermediate film (8) can be rotated on the carrier film (2*b*), particularly by 90°.

* * * * *